United States Patent [19]

Yamamoto

[11] 4,350,761

[45] Sep. 21, 1982

[54] METHOD OF AND REAGENTS FOR QUANTITATIVE ANALYSIS OF CYCLIC NUCLEOTIDES

[75] Inventor: Itaru Yamamoto, Okayama, Japan

[73] Assignee: Yamasu Shoyu Kabushiki Kaisha, Chiba, Japan

[21] Appl. No.: 149,959

[22] Filed: May 15, 1980

[30] Foreign Application Priority Data

May 18, 1979 [JP] Japan .................................. 54-61669

[51] Int. Cl.$^3$ ...................... G01N 33/54; C12Q 1/00; C12N 9/96
[52] U.S. Cl. ........................................ 435/7; 435/188; 435/810; 23/230 B; 424/12
[58] Field of Search .................. 435/4, 7, 188, 177, 435/176, 810, 184; 424/1, 1.5, 8, 12; 23/230 B

[56] References Cited

U.S. PATENT DOCUMENTS

| | | | |
|---|---|---|---|
| 3,839,153 | 10/1974 | Schuurs et al. | 435/188 |
| 3,850,752 | 11/1974 | Schuurs et al. | 435/188 |
| 3,852,157 | 12/1974 | Rubenstein et al. | 435/188 |
| 4,171,432 | 10/1979 | Carrico et al. | 435/7 |

OTHER PUBLICATIONS

Van Weeman et al., "Immunoassay Using Hapten-Enzyme Conjugates", *FEBS Letters*, vol. 29, No. 1 (1972), pp. 77-81.

Meyerhoff et al., "Electrode-Based Enzyme Immunoassays Using Urease Conjugate", *Methods in Enzymology*, vol. 70, (1980), pp. 439-454.

Dray, et al., "Enzyme Immunoassay of Progesterase in the Picogram Level Using B-Gahactosidnase as Laskel", *Biochim Biophys Acta*, vol. 403, (1975), pp. 131-138.

Wisdom, Enzyme Immunoassay, *Clin. Chem*, vol. 22, No. 8 (1976), pp. 1243-1255.

Goldberg, "Radio immunoassay for Adenosine 3', 5'--Cyclic Monophosphate and Guanosine-3', 5'-Cyclic Monophosphlate in Human Blood, Urine, and Cerebrospinal Fluid", *Clin. Chem*, vol. 23, No. 3, (1977), pp. 576-580.

*Primary Examiner*—Thomas G. Wiseman
*Attorney, Agent, or Firm*—Wenderoth, Lind & Ponack

[57] ABSTRACT

A method of quantitative analysis of cyclic nucleotides which comprises: acylating a cyclic nucleotide in an assay sample by using an acylating agent; causing said acyl-cyclic nucleotide and a specific quantity of an enzyme-labeled cyclic nucleotide formed by bonding a cyclic nucleotide corresponding to the acyl-cyclic nucleotide and an enzyme through a dicarboxylic acid to undergo competitive reaction with a specific quantity of an antibody with respect to a corresponding cyclic nucleotide; separating the enzyme-labeled cyclic nucleotide which has become bonded to said antibody and the enzyme-labeled cyclic nucleotide which has not become bonded thereto; and determining the quantity of the cyclic nucleotide by measuring the enzyme activity of either of the enzyme-labeled cyclic nucleotides. For this analysis, a reagent comprising an enzyme-labeled cyclic nucleotide is used.

12 Claims, 2 Drawing Figures

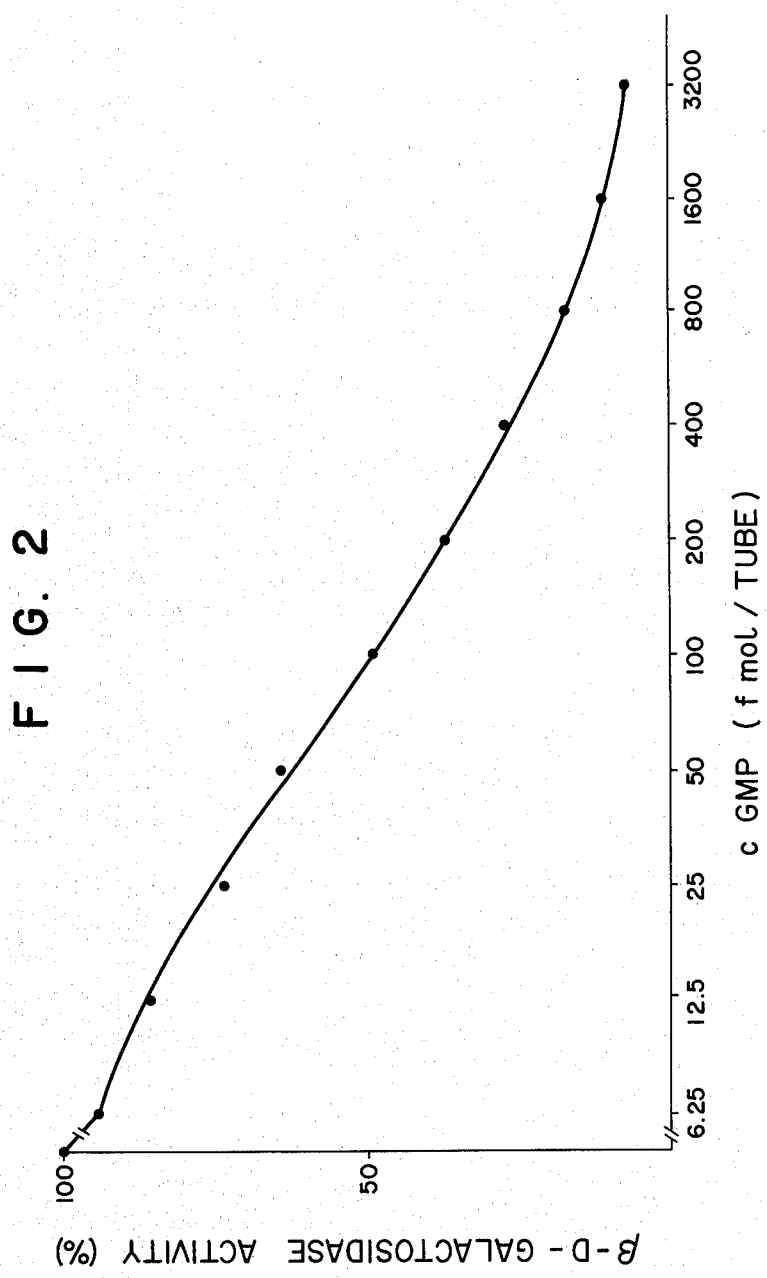

METHOD OF AND REAGENTS FOR QUANTITATIVE ANALYSIS OF CYCLIC NUCLEOTIDES

BACKGROUND OF THE INVENTION

This invention relates to a method of quantitative analysis of cyclic nucleotides depending on the enzyme immunoassay method (hereinafter referred to by the abbreviation EIA) and to reagents therefor.

In recent years, adenosine-3',5'-cyclic monophosphate (hereinafter referred to by the abbreviation cAMP) has been widely studied as a mediator of hormone action, and its physiologic actions with respect to guanosine-3',5'-cyclic monophosphate (cGMP), inosine-3',5'-cyclic monophosphate (cIMP), gytidine-3',5'-cyclic monophosphate (cCMP), and uridine-3',5'-cyclic monophosphate (cUMP) (hereinafter referred to respectively by the indicated abbreviations) are being clarified.

Particularly in the case where a living body assumes an unphysiologic or pathologic state such as that due to a disease, the contents of cAMP and cGMP in the cells or body fluids of that living body fluctuate. From this observation, the measurement of these contents within living bodies is being increasingly regarded to be of important significance not only in the basic medical research field but also for diagnosis, prevention, and treatment of diseases in the field of clinical medicine. For example, the determination of the contents of cAMP and cGMP in living body samples such as leucocytes of asthmatic patients, skins of psoriasis patients, blood platelets of thrombocytosis patients, blood and urine of psuedohypoparathyroidism patients, and cerebrospinal fluid of manic-depressive psychotic patients is considered to be effective in the diagnosis and treatment of these diseases. Furthermore, it is predictable that the relationships between these cyclic nucleotides and a large number of disease conditions will become clear in the future. Accordingly, there is a deep significance in the establishment of simple, convenient, and highly accurate methods of quantitatively determining cyclic nucleotides.

One of the methods of quantitative analysis of cyclic nucleotides such as cAMP and cGMP known heretofore is the so-called radioimmunoassay method (hereinafter referred to by the abbreviation RIA method). This RIA method comprises causing a cyclic nucleotide in a living body sample and a cyclic nucleotide labeled with a radioisotope to react competitively with a corresponding antibody and measuring the quantity of radiation of the radioisotope-labeled cyclic nucleotide which has bonded with the antibody or the radioisotope-labeled cyclic nucleotide which has not bonded with the antibody thereby to determine the quantity of the cyclic nucleotide.

The quantitative analysis with very high accuracy of cyclic nucleotides by applying to this RIA method such methods as the method in which a cyclic nucleotide is succinylated thereby to improve its affinity for an antibody obtained when cyclic nucleotide-succinyl albumin is used as an antigen and the method of using an imidazole buffer solution for the reaction medium of an antigen-antibody reaction thereby to increase the bonding rate, the sensitivity, and the stability of the bonded product is being reduced to practice, for example, as disclosed in Biochemical Medicine, Vol. 18, pp. 257–273, (1977).

These RIA methods, however, are accompanied by various problems basically arising from the use of radioisotopes. For example, there is the danger of harm to the human body and environmental pollution due to radiation. Another problem is the need for special facilities and equipment for preventing the diffusion of radiation. Still other problems are the need for expensive measuring apparatus for measuring radiation, the requirement for a qualification for handling radioisotopes, and the inconvenience of handling, transportation, and preservation of radioisotopes due to their instability, in general.

Recently, with the aim of solving these problems accompanying the RIA method, EIA methods in which enzymes are used as labels instead of radioisotopes have been studied and developed. Some are known to have already been reduced to practice as quantitative analysis methods for α-fetoprotein, HBs antigen, carcinoembryonic antigen, thyroxine, digoxin, IgE, etc. However, with regard to quantitative analysis by the EIA method of cyclic nucleotides, there has been no report whatsoever.

The present inventor has carried out research with the object of developing a method depending on the EIA method for quantitative analyses of cyclic nucleotides. As a result, the inventor has succeeded in perfecting a method which, in sensitivity, accuracy, and reproducibility is comparable to or superior to the RIA method.

SUMMARY OF THE INVENTION

According to this invention in one aspect thereof, briefly summarized, there is provided a method of quantitative analysis of cyclic nucleotides which comprises:

acylating a cyclic nucleotide in an assay sample by using an acylating agent;
causing said acyl-cyclic nucleotide and a specific quantity of an enzyme-labeled cyclic nucleotide formed by bonding a cyclic nucleotide corresponding to said acyl-cyclic nucleotide and an enzyme through a dicarboxylic acid to undergo competitive reaction with a specific quantity of an antibody to the corresponding cyclic nucleotide;
separating the enzyme-labeled cyclic nucleotide which has become bonded to said antibody and the enzyme labeled cyclic nucleotide which has not become bonded thereto; and
determining the quantity of the cyclic nucleotide by measuring the enzyme activity of either of said enzyme-labeled cyclic nucleotides.

According to this invention in another aspect thereof, there are provided reagents for quantitative analysis of cyclic nucleotides by the method according to this invention, each of the reagents comprising an enzyme-labeled cyclic nucleotide.

According to this invention in a further aspect thereof, there are provided reagents for quantitative analysis of cyclic nucleotides by the method according to this invention, each of the reagents comprising an antibody to a cyclic nucleotide immobilized on an insoluble carrier.

According to this invention in a still further aspect thereof, there are provided reagent kits for quantitative analysis of cyclic nucleotides, the principal kits A, B, C, and D respectively comprising the following items in combination.

A. A kit for quantitative analysis of cyclic nucleotides comprising, in combination:

(a) an enzyme-labeled cyclic nucleotide;
(b) an antibody to a cyclic nucleotide immobilized on an insoluble carrier;
(c) an acid anhydride;
(d) an organic tertiary amine;
(e) a buffer solution;
(f) a cyclic nucleotide standard solution;
(g) an enzyme substrate; and
(h) a reaction terminating agent.

B. A kit for quantitative analysis of cyclic nucleotides comprising, in combination:

(a) an enzyme-labeled cyclic nucleotide;
(b) an antibody to a cyclic nucleotide immobilized on an insoluble carrier;
(c) an acid anhydride;
(d) an organic tertiary amine;
(e) a buffer solution;
(f) a cyclic nucleotide standard solution;
(g) an enzyme substrate;
(h) a reaction terminating agent; and
(i) a phosphodiesterase inhibitor.

C. A kit for quantitative analysis of cyclic nucleotides comprising, in combination:

(a) an enzyme-labeled cyclic nucleotide;
(b) an antibody to a cyclic nucleotide;
(b') a separation agent;
(c) an acid anhydride;
(d) an organic tertiary amine;
(e) a buffer solution;
(f) a cyclic nucleotide standard solution;
(g) an enzyme substrate; and
(h) a reaction terminating agent.

D. A kit for quantitative analysis of cyclic nucleotides comprising, in combination:

(a) an enzyme-labeled cyclic nucleotide;
(b) an antibody to a cyclic nucleotide;
(b') a separation agent;
(c) an acid anhydride;
(d) an organic tertiary amine;
(e) a buffer solution;
(f) a cyclic nucleotide standard solution;
(g) an enzyme substrate;
(h) a reaction terminating agent; and
(i) a phosphodiesterase inhibitor.

According to the present invention, it is possible to carry out ultramicroassay of cyclic nucleotides with high acuracy, and thanks to its highly improved sensitivity it is possible to use a small quantity of a sample highly diluted whereby it is thus possible to carry out the assay repeatedly on the very same cyclic nucleotide or the assay of a plurality of cyclic nucleotides concurrently. Furthermore, it is possible to subject to assay a sample of body fluid such as urine or blood without deproteination or a sample of acid-extracts of living body tissues without pretreatment such as chromatography.

In accordance with the best mode of the present invention, it is possible to carry out quantitative analysis of cyclic nucleotides in a concentration up to at least 0.5 f mol. EIA method with such high sensitivity on lower molecular compounds such as cyclic nucleotides is not believed to have heretofore been known.

The nature, utility, and further features of this invention will be more clearly apparent from the following detailed description beginning with a consideration of the general features and details of the invention and concluding with specific examples of practice thereof.

BRIEF DESCRIPTION OF THE DRAWING

In the drawing:

FIG. 2 is a graph showing the calibration curve of cGMP obtained in Example 2.

DETAILED DESCRIPTION OF THE INVENTION

Figure 1:
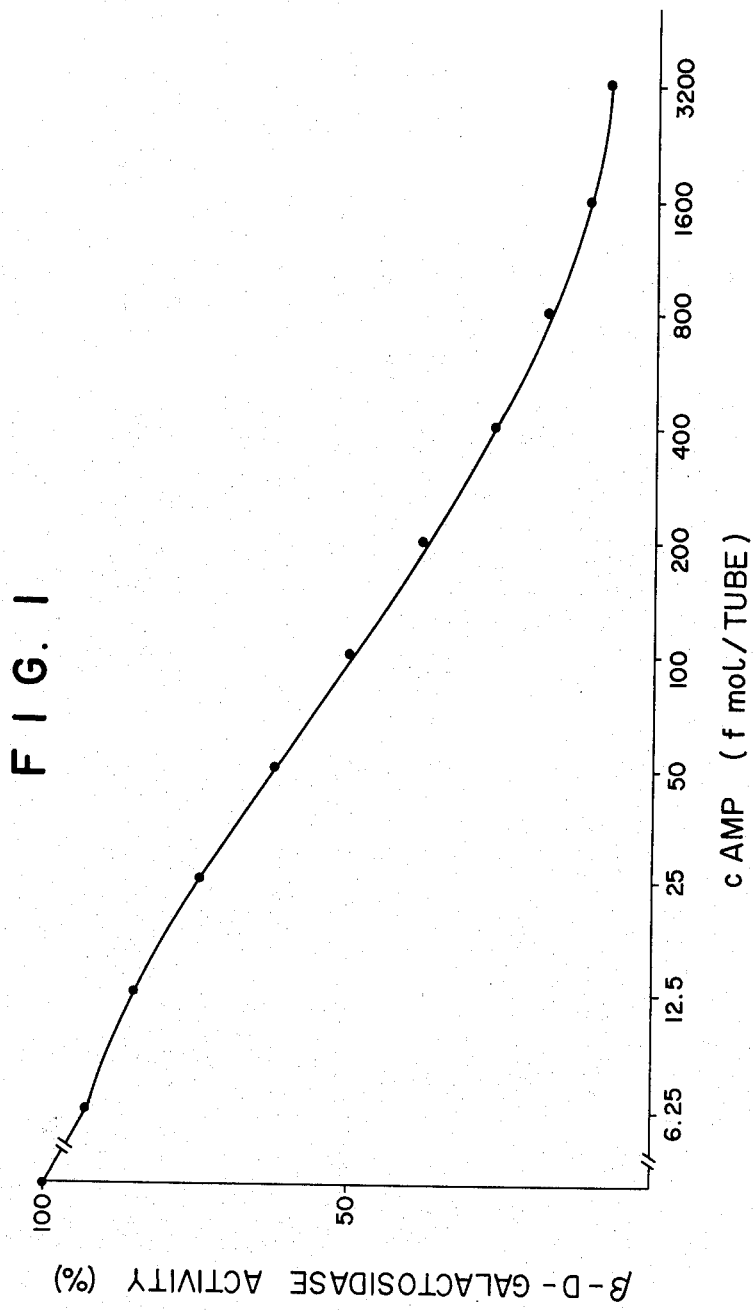
FIG. 1 is a graph showing the calibration curve of cAMP obtained in Example 1 of the method of this invention.

In this invention, the term "cyclic nucleotides" is used to designate collectively cAMP, cGMP, cIMP, cCMP, and cUMP. Furthermore, the term "acyl-cyclic nucleotide" designates a 2'-O-acyl derivative of a cyclic nucleotide.

1. Preparation of assay sample

There are no particular restrictions relating to the preparation of samples from the living bodies. Body fluids such as blood, cerebrospinal fluid, and urine do not require pretreatment and can be subjected directly to assaying, but, in order to prevent decomposition of cyclic nucleotides during the assaying operation due to phosphodiesterase in the sample, it is preferable to add a phosphodiesterase inhibitor of suitable concentration into the sample. Specific examples of phosphodiesterase inhibitors are ethylenediaminetetraacetic acid (EDTA) and theophylline. The concentration in which EDTA is used is ordinarily 5 to 10 mM as a final concentration. In the case of a blood sample, the supernatant (plasma) obtained by ordinary centrifugal separation is used as a sample for assaying.

The general tissue is prepared as an aqueous extract prepared by extraction by an acid (for example, hydrochloric acid, perchloric acid, or trichloroacetic acid), or by an alkali (for example, barium hydroxide-zinc sulfate), or by a hydrophilic organic solvent.

2. Acylation Reaction 2-1: Acylating Reagent

For the acylating agent, an acid anhydride and an organic tertiary amine are used. These are mixed and used immediately prior to the operation of the acylation reaction.

The kind of the acid anhydride to be used is selected from anhydrides of dicarboxylic acids corresponding to the dicarboxylic acid residue of an antigen (resulting from the bonding of a cyclic nucleotide and a carrier protein through a dicarboxylic acid) used in the production of the antibody with respect to a cyclic nucleotide or from anhydrides of similar mono- or dicarboxylic acids thereto. The antigen is expressed by the following formula.

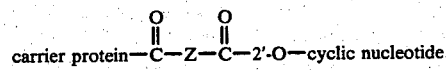

The symbol Z of the dicarboxylic acid residue moiety represents an alkylene of 1 to 8 carbon atoms, an alkenylene of 2 to 6 carbon atoms, an alkynylene of 2 to 6 carbon atoms, a cycloalkylene of 4 to 10 carbon atoms, an arylene of 6 to 10 carbon atoms, an oxaalkylene of 4 to 8 carbon atoms, an azaalkylene of 4 to 8 carbon atoms, or the like. Of these, the alkylenes of 1 to 8 carbon atoms are preferable, and the most generally used are those of succinic acid residue and glutaric acid residue in which Z is an alkylene of two and three carbon atoms, respectively. For the acid anhydride in the case where the dicarboxylic acid residue is succinic acid residue, other than succinic anhydride corresponding thereto, similar mono- or dicarboxylic acid anhydrides having an alkyl or alkylene moiety of 1 to 4 carbon atoms such as acetic anhydride, propionic anhydride, butyric anhydride, and malonic anhydride are used.

As for the form in which the acid anhyride is prepared, it may be in a powder state, but a solution thereof in an organic solvent is preferable since, then, its miscibility with organic tertiary amines and assay samples will be excellent, and its handling will be facilitated. For the organic solvent, a solvent which stably dissolves acids and, moreover, does not impart a harmful effect on the antigen-antibody reaction and the labeling enzyme activity is satisfactory. Specific examples of such organic solvents are acetone, pyridine, dioxane, acetonitrile, dimethylsulfoxide, diethylene glycol dimethyl ether, hexamethyl phosphoric triamide, tetrahydropyrane, and methyl cellosolve acetate. Acetone is particularly suitable for use in this invention.

While the quantity in which the acid anhydride is used is determined by its kind, in the case of succinic anhydride, for example, this quantity relative to 100 µl of the sample is ordinarily 2 to 6 mg, preferably 3.5 to 4.5 mg. It has been found that when this quantity of the acid anhydride becomes excessive, undesirable consequences such as deposition of the acid anhydride in the acylation reaction system occur, and there is the possibility of the subsequent processes such as antigen-antibody reaction being adversely affected.

An organic tertiary amine which is readily and uniformly miscible with the solution of the acid anhydride in the organic solvent and the assay sample, does not adversely affect the antigen-antibody reaction, and promotes the acylation reaction is suitable for use in the invention. Examples of organic tertiary amines which may be effectively utilized are aliphatic tertiary amines such as triethylamine, tri-n-butylamine and the like, and heterocyclic bases such as 4-morpholino-N,N'-dicyclohexyl carboxamidine, pyridine, trimethylpyridine, quinoline, 1,8-diazabicyclo[5,4,0]undecene-7, and the like, triethylamine and 4-morpholino-N,N'-dicyclohexyl carboxamidine being preferable examples. The quantity in which the organic tertiary amine is used is, in the case of triethylamine, for example, ordinarily 15 µl or less, preferably 10 µl or less relative to 100 µl of the sample. An excessive quantity of the organic tertiary amine causes the pH value to rise and impair the acylating reaction.

2-2: Acylation reaction conditions

The acylation reagent prepared by blending the acid anhydride and the organic tertiary amine is added to the assay sample, and the acylation reaction is caused to proceed. The reaction conditions are not particularly limited. For example, in the case of a succinylation reaction, the conditions of a reaction time of 5 to 60 minutes at room temperature are ordinarily sufficient.

3. Competitive antigen-antibody reaction 3-1: Enzyme-labeled cyclic nucleotide

The preferable properties of an enzyme for labeling the antigen in the EIA method are as follows.

3-1-1: The enzyme itself has a high specificity and is soluble.

3-1-2: The same enzyme does not exist in the assay sample.

3-1-3: The substrate, an enzyme-inhibiting substance or another disturbing factor does not exist in the assay sample.

3-1-4: An enzyme which acts competitively on the same substrate does not exist in the assay sample.

3-1-5: The enzyme is stable for a long time under ordinary conditions of preservation in dry state or in solution.

3-1-6: An easily detectable substance is formed by the enzyme reaction, and, moreover, the detection of this substance is not disturbed by another substance coexisting in the assay system.

3-1-7: The activity of the enzyme after it has bonded to the ligand is high.

Examples of enzymes which are known to satisfy these conditions relatively well and to be suitable for use in the EIA method are $\beta$-D-galactosidase, peroxidase, alkaline phosphatase, glucose oxidase, glucoamylase, lysozyme, malate dehydrogenase, glucose-6-phosphate dehydrogenase, and acetylcholine esterase. In addition, lipase, $\beta$-glucuronidase, hyaluronidase, $\beta$-glucosidase, and others may be considered. Recently, a method of utilizing an active fragment of an enzyme also has been reported (in Japanese Patent Laid Open Publication No. 9316/1978). Of these enzymes, $\beta$-D-galactosidase is most preferable because, with its use, the formed products of the enzyme reaction can be assayed with higher sensitivity, and because an enzyme preparation of high purity in which the enzyme, itself, has high stability and specific activity is readily available.

A cyclic nucleotide and an enzyme for labeling an antigen are bonded through a dicarboxylic acid similarly as in the case of an antigen used in the production of an antibody. The bonding method generally used comprises first linking through an ester linkage the 2'-hydroxyl group of the cyclic nucleotide and one of the carboxyl groups of the dicarboxyl acid by an ordinary acylation reaction and then causing the other free carboxyl group of the dicarboxylic acid residue of this acyl-cyclic nucleotide and the amino group of the enzyme for labeling the antigen to undergo condensation.

There is no special restriction regarding the method of condensation of the acyl-cyclic nucleotide and the enzyme for labeling the antigen. Any suitable method which will not lower the enzyme activity of the enzyme for labeling may be used. One specific example of a suitable method is the acid anhydride method which comprises reacting an alkyl chloroformate such as ethyl chloroformate or isobutyl chloroformate with the acyl-cyclic nucleotide in the presence of a base such as, for example, triethylamine thereby to form mixed anhydrides and causing this and the enzyme to act.

Another specific example of a suitable condensation method is the carbodiimide method in which the acyl-cyclic nucleotide and the enzyme for labeling the antigen are caused to react in the presence of a carbodiimide reagent. Examples of suitable carbodiimide reagents are dicyclohexylcarbodiimide (DCC), 1-ethyl-3-(3- dimethylaminopropyl)-carbodiimide (EDC), 1-ethyl-3-(3-diethylaminopropyl)-carbodiimide, 1-cyclohexyl-3-(2-morpholinoethyl)-carbodiimide, 1-cyclohexyl-3-(4-diethylaminocyclohexyl)-carbodiimide, and N-methyl-N,N'-di-tert-butylcarbodiimidium tetrafluoroborate. The use of condensation agents other than those enumerated above such as, for example, N-ethyl-5-phenylisoxazolium-3'-sulfonate (Woodward's reagent K), is not excluded provided that it is not counter to the objects of this invention. The condensation reaction conditions are selected according to normal practice.

Still another possible method utilizes an Ugi reaction which is caused by adding an isocyanide such as 3-(dimethylamino)propyl isocyanide and an aldehyde such as acetaldehyde or a ketone compound to a mixture solution of the acyl-cyclic nucleotide and the enzyme for labeling the antigen.

3-2:Antibody to the cyclic nucleotide

The antibody to the cyclic nucleotide is prepared by a method which comprises immunizing animals such as rabbits, horses, sheep, cattle, and rats with an antigen produced by causing the cyclic nucleotide to bond with a carrier protein as described hereinbefore through a dicarboxylic acid. Examples of applicable carrier proteins are serum albumin, globulin, hemocyanin, ovalbumin, and fibrinogen. Of these, serum albumin is generally used. For example, the method of causing succinyl-cyclic nucleotide to bond with human serum albumin and using this to immunize rabbits, horses, cattle, etc. (as disclosed in *The Journal of Biological Chemistry*, Vol. 247, No. 4 (pp. 1106–1113 (1972)) is known. An antiserum obtained in this manner is used as the antibody.

Furthermore, an antibody purified and isolated from an antiserum may be used. In addition, an antibody active fraction such as an F (a b')$_2$ fragment obtained by an enzyme treatment such as pepsin treatment of an antibody and an F a b' fragment obtained by treatment of the antibody with a reducing agent such as 2-mercaptoethylamine can be used.

The antibody is prepared as solutions in any of various buffer solutions for use in the EIA method based on the liquid-phase method but is prepared by immobilizing such on an insoluble carrier for use in the EIA method based on the solid-phase method. The solid-phase method is advantageous because of facility of the analysis procedure.

For the insoluble carrier on which the antibody is to be immobilized, any of those generally used in the EIA method is applied. Specific examples of such insoluble carriers are silicone, glass, ceramics, polystyrenes, cross-linked polyacrylamides, plastics, CM cellulose, DEAE cellulose, cellulose, cross-linked dextran, and filter paper. If desired, the carriers may be used after their surfaces have been coated with an organic silane derivative, specific examples of which are γ-mercaptopropyltrimethoxysilane, γ-aminopropyltriethoxysilane, N-β-aminoethyl-γ-aminopropyltrimethoxysilane, N-β-aminoethyl-α-methyl-γ-aminopropyldimethoxymethylsilane, and N-bis-β-hydroxyethyl-γ-aminopropyltriethoxysilane. The shape or form of the carrier is not especially limited; it may be in the form of pellets, particles, rods, sheets, spheres, or the like.

The antibody may be immobilized on the insoluble carrier by any known method. For example, a method wherein the antibody is caused to be directly and physically adsorbed on the insoluble carrier or a method wherein the antibody is bonded through a bifunctional chemical bonding agent such as glutaraldehyde, 2,2-dipyridyl sulfide, or p,p'-difluoro-m,m'-dinitrodiphenyl sulfone is applied.

Particularly, a coated carrier obtained by the method wherein the antibody is caused to be physically adsorbed on a silicone carrier or a carrier which has been coated with an organic silane derivative is advantageous in that the non-specific bond of the enzyme bound ligand is inhibited, the quantity of the antibody immobilized on it is constant, and, at the same time, the immobilization is accomplished very stably, whereby excellent assaying sensitivity, accuracy, and reproducibility are attained.

3-3: Antigen-antibody reaction

After the acylation reaction, the assay sample is ordinarily diluted 5 to 6 times by using a buffer for dilution. For the cyclic nucleotide standard solution, the standard stock solution is acylated and thereafter successively and multiplicatively diluted by using a buffer for dilution and is thus used for assaying.

For the buffer for dilution, any buffer which will cause the antigen-antibody reaction to proceed stably can be applied, there being no especial limitation as to its kind. In this invention, for example, a 0.1 M sodium phosphate buffer solution (pH 6.9) containing 0.1 M sodium chloride, 1 mM magnesium chloride, and 0.1–0.3-percent bovine serum is suitable for use, but, in addition, buffers such as a trishydrochloride buffer, an acetate buffer, a citratephosphate buffer, and an imidazole buffer, which are applicable in the EIA method can be used.

The antigen-antibody reaction is carried out by adding the assay sample and a specific quantity of the enzyme-labeled cyclic nucleotide, either simultaneously or one after the other, with respect to a specific quantity of an antibody immobilized on an insoluble carrier or a soluble antibody.

The reaction conditions differ with factors such as the kind of the acylation agent used and the preparation of the antibody, but, ordinarily, are a temperature of 1° to 5° C. and a time of 6 to 48 hours.

The type of the enzyme-labeled cyclic nucleotide and antibody are selected of course depending on the type of cyclic nucleotide to be analyzed. In the case where a plurality of cyclic nucleotides are to be analyzed in the same single batch simultaneously, a mixture of cyclic nucleotides which are corresponding to the cyclic nucleotides to be analyzed and which have been labeled with different enzymes is used as the enzyme-labeled cyclic nucleotide thereby to cause each of the antigen-antibody reactions to take place concurrently for each of the cyclic nucleotides.

4. Measurement of enzyme activity

After completion of the antigen-antibody reaction, the enzyme-labeled cyclic nucleotide (hereinafter referred to as "B") which has been bonded to the antibody and the enzyme-labeled cyclic nucleotide (hereinafter referred to as "F") which has not been bonded to the antibody are separated by an ordinary method, and the enzyme activity of either is measured.

In the case of the solid-phase method, the separation of "B" and "F" can be readily carried out by a method such as aspiration, decantation, or filtration. In the case of the liquid-phase method, the separation is carried out by a method employing a suitable separation agent. As applicable separation methods, there are, for example, the double antibody method which comprises preparing a second antibody to the cyclic nucleotide antibody or the F (a b')₂ or F a b' fragment in another animal and using the second antibody thus obtained to cause precipitation of "B", and a salting out method for fractioning "B" and "F" by using ammonium sulfate.

For measurement of the enzyme activity, a method suitable for the objects of the invention in accordance with the kind of the enzyme for labeling the antigen is used. For known methods of measuring the enzyme activity, there are references such as Guilbault, George G.: Handbook of Enzymatic Methods of Analysis; Clinical and Biochemical Analysis, Vol. 4, Marcel Dekker, Inc., 1976.

In the case where $\beta$-D-galactosidase is used for the enzyme for labeling the antigen, there is a method wherein, with the use of 4-methylumbelliferyl-$\beta$-D-galactoside as the enzyme substrate, the fluorescence intensity of 4-methylumbelliferone formed by the enzyme reaction is measured by a fluorometer at 360 nm for excitation and at 450 nm for emission. As other assay methods of $\beta$-D-galactosidase depending on the fluorescence, there are known, for example, the method of measuring the fluorescence of 6-hydroxyfluorane by using 6-hydroxyfluorane-$\beta$-D-galactopyranoside as a substrate and the method of measuring the fluorescence of fluorescein by using fluorescein-di-$\beta$-D-galactopyranoside as a substrate. Further, there are spectrophotometric methods such as a method wherein o-nitrophenyl-$\beta$-D-galactoside is used as a substrate, and the o-nitrophenol produced by an enzyme reaction is subjected to colorimetry.

From the measured values of the standard solution of the cyclic nucleotide, a calibration curve is obtained, and the cyclic nucleotide in the assay sample is determined.

5. Reagent kit for quantitative analysis

In order to practice the method of this invention in a simple and convenient manner, a number of kinds of reagents indispensible for its practice are combined in a kit. As a kit for assaying by the solid-phase method, a combination of reagents as set forth below is made available.

(a) Enzyme-labeled cyclic nucleotide
(b) Antibody for a cyclic nucleotide immobilized on an insoluble carrier
(c) Acid anhydride
(d) Organic tertiary amine
(e) Buffer solution
(f) Cyclic nucleotide standard solution
(g) Enzyme substrate
(h) Reaction terminating agent.

According to the necessity, (i) Phosphodiesterase inhibitor and other reagents are also combined in the kit.

In the case of a kit for analysis of a single cyclic nucleotide, the reagents (a), (b) and (f) are so selected that the cyclic nucleotides in these reagents are the same as the cyclic nucleotide to be analyzed. In the case of a kit for simultaneous analysis of a plurality of cyclic nucleotides, the reagent (a) for the cyclic nucleotides is provided separately in the kit for each of the cyclic nucleotides, or the reagents are mixed to form lots for each of the cyclic nucleotides. This applies also for the reagents (b) and (f). In the case where a plurality of cyclic nucleotides are to be analyzed in the same single batch simultaneously, the labeling enzymes in reagent (a) must be selected depending on the types of the cyclic nucleotides to be analyzed. Enzyme substrates for reagent (g) are to be selected depending on the types of the labeling enzymes selected. The buffer solution of reagent (e) can also be provided in separate packages respectively of a buffer for dilution and a buffer for washing. For the reaction terminating agent of reagent (h), an agent which can stop the enzyme reaction is satisfactory and is appropriately selected according to the characteristics of the enzyme for labeling. For example, alkaline reagents such as sodium carbonate and glycinesodium hydroxide solution and acidic reagents such as hydrochloric acid are used.

As a kit for the liquid-phase method, a soluble antibody is substituted for reagent (b) among the above enumerated reagents of the kit for the solid-phase method, and, further, a separation agent is combined as reagent (b') in the kit.

6. Examples

In order to indicate more fully the nature and utility of this invention, the following specific examples of practice are set forth, it being understood that these examples are presented as illustrative only and that they are not intended to limit the scope of the invention.

Example 1

Determination of cAMP 6-1-1: Forming of $\beta$-D-galactosidase-labeled succinyl.cAMP 4.29 mg of 2'-O-succinyl-cAMP was dissolved in 500 $\mu$l of a 0.01 M sodium phosphate buffer solution (pH 6.0) containing 0.15 M of sodium chloride, 1 mM magnesium chloride (hereinafter referred to as buffer A). Into the resulting solution, 50 $\mu$l ($5 \times 10^{-5}$ mol) of $\beta$-D-galactosidase (mfd. by Sigma Inc.) was blended, and thereafter 5 mg of 1-ethyl-3-(3-dimethylaminopropyl) carbodiimide was added, the mixture being caused to react at 4° C. for 3 hours. The reaction liquid was dialyzed against the buffer A, and $\beta$-D-galactosidase-labeled succinyl-cAMP was prepared.

6-1-2: Preparation of antibody immobilized on silicone disc

Using a punch, small silicone discs (each of 6-mm diameter, 1-mm thickness, and 33.0 to 38.0-mg weight) were obtained from a silicone sheet. These discs were thoroughly washed in Haemo-sol washing solution, hot water, and distilled water, dried, weighed, and divided into 11 groups by weight in steps of 0.5 mg.

One group of the silicone discs was immersed in a 0.05 M sodium phosphate buffer solution of antisuccinyl-cAMP rabbit blood serum and was thus left at 4° C. for 24 hours. The silicone discs thus treated were then washed with 0.01 M sodium phosphate buffer solution of pH 6.9 containing 0.1 percent of bovine blood serum albumin, 1 mM magnesium chloride, and 0.1 M sodium chloride (hereinafter referred to as buffer B).

6-1-3: Preparation of succinylating agent 200 mg of succinic anhydride was dissolved in 4.5 ml of acetone, and with the resulting solution, 0.5 ml of triethylamine was blended.

6-1-4: Preparation of succinylated cAMP standard solution 4 ml of 0.1 M buffer B, 0.5 ml of the succinylating agent, and 0.5 ml of redistilled water were blended well thereby to prepare a buffer solution for dilution of the standard solution.

50 μl of a cAMP standard stock solution (320 pmol/ml) was placed into a small test tube (No. I), and 50 μl of the succinylating agent was added to and mixed with this standard stock solution. The resulting solution was left at room temperature for 10 minutes, and thereafter 400 μl of 0.1 M buffer B was added thereto thereby to prepare a succinyl cAMP standard solution. 250 μl of the buffer solution for dilution of the standard solution was placed in each of nine small test tubes (Nos. II through X). 250 μl of the succinyl cAMP standard solution was added to test tube No. II and blended with the buffer solution. Thereafter, multiplicative dilution was successively carried out thereby to prepare succinyl cAMP standard solutions of the following respective concentrations (/100 μl).

| | | | |
|---|---|---|---|
| 3,200 f mol | (No. I) | 1,600 f mol | (No. II) |
| 800 f mol | (No. III) | 400 f mol | (No. IV) |
| 200 f mol | (No. V) | 100 f mol | (No. VI) |
| 50 f mol | (No. VII) | 25 f mol | (No. VIII) |
| 12.5 f mol | (No. IX) | 6.25 f mol | (No. X) |

6-1-5: Preparation and succinylation of an assay sample

Human whole blood was added to and mixed with 500 mM EDTA aqueous solution in a proportion of 1 ml of the former to 10 μl of the latter. The resulting mixture was immediately subjected to centrifuging at 4° C. and 2,000 rpm for 5 minutes, and 50 μl of the resulting supernatant was taken in a test tube. 50 μl of the succinylating agent was added and mixed with this supernatant, and the mixture thus obtained was left at room temperature for 10 minutes. Thereafter, 400 ml of 0.1 M buffer B was added to the mixture.

6-1-6: Assaying procedure

Small test tubes were prepared as follows.

Stand. sol. (Nos. I through X): 20 test tubes, Nos. 1,1′ to 10,10′
For zero use: 2 test tubes, Nos. 11,11′
For blank use: 2 test tubes, Nos. 12,12′
For assaying the sample: 2 test tubes, Nos. 13,13′

In each of the small test tubes other than those for the blank, one antibody-coated silicone disc prepared in 6-1-2 was placed. In each of the small test tubes for blank use, a small piece of silicone of the same weight which had been subjected to only the treatment with the buffer B was placed. 100 μl of the buffer solution for dilution of the standard solution was added to each of the test tubes for zero use (Nos. 11,11′) and for blank use (Nos. 12,12′), and 100 μl of each of the succinyl cAMP standard solution (Nos. I through X) was added to each of the test tubes for standard solution use (Nos. 1,1′ through 10,10′). 100 ml of the succinylated assay sample was added to each of the test tubes for assaying the sample (Nos. 13,13′).

100 ml of a dilute solution of succinyl cAMP labeled with β-D-galactosidase was added to each of the test tubes, and each test tube was then left at 4° C. for 24 hours.

The reaction liquid in each test tube was drawn out with an aspirator, and, by adding 1 ml of 0.01 M buffer B into each test tube, the silicone disc or piece was washed. The resulting washing was then drawn out with the aspirator. This washing procedure was repeated.

Each of the silicon discs or pieces was transferred into a medium-sized test tube, and 100 μl of 0.01 M buffer B was added each medium-sized test tube. 50 μl of 4-methylumbellifery-β-D-galactoside was added to and mixed with the contents of each test tube. The resulting mixture in each test tube was subjected to incubation at 30° C. for 30 minutes.

2.5 ml of 0.1 M glycine-sodium hydroxide solution (pH 10.3) was added into each test tube thereby to terminate the enzyme reaction. Then the 4-methylumbelliferone liberated was measured by a fluorometer at 360 nm for excitation and at 450 nm for emission. The results obtained are shown in Table 1. The calibration curve is shown in FIG. 1.

TABLE 1

| Assay sample | Specific activity (%) | β-D-galactosidase activity (μ unit/tube) |
|---|---|---|
| Blank | 0 | — |
| Zero | 100 | 178 |
| Stand. solution | | |
| 6.25 fmol | 93 | 166 |
| 12.5 | 85 | 151 |
| 25 | 74 | 132 |
| 50 | 62 | 110 |
| 100 | 50 | 89 |
| 200 | 38 | 68 |
| 400 | 26 | 46 |
| 800 | 18 | 32 |
| 1,600 | 11 | 20 |
| 3,200 | 8 | 14 |
| Whole blood sample | 35 | 62 |

EXAMPLE 2

Determination of cGMP 6-2-1 through 6-2-6:

Determination of cGMP was carried out by the procedure described in Example 1 except for the use of 2′-O-succinyl-cGMP in place of 2′-O-succinyl-cAMP, the use of anti-succinyl-cGMP rabbit blood serum in place of anti-succinyl-cAMP rabbit blood serum, and the use of cGMP standard stock solution in place of cAMP standard stock solution. The measured values are set forth in Table 2. The calibration curve is shown in FIG. 2.

TABLE 2

| Assay sample | Specific activity (%) | β-D-galactosidase activity (μ unit/tube) |
|---|---|---|
| Blank | 0 | — |
| Zero | 100 | 150 |
| Stand. solution | | |
| 6.25 f mol | 94 | 141 |
| 12.5 | 85 | 128 |
| 25 | 73 | 110 |
| 50 | 64 | 96 |
| 100 | 49 | 74 |
| 200 | 37 | 56 |
| 400 | 27 | 41 |
| 800 | 17 | 26 |
| 1,600 | 11 | 17 |
| 3,200 | 9 | 14 |
| Whole blood sample | 68 | 102 |

What is claimed is:

1. A method for the quantitative analysis of cyclic nucleotides which comprises:
   acylating a cyclic nucleotide in an assay sample by using an acylating agent;

causing said acyl-cyclic nucleotide and a predetermined quantity of an enzyme-labeled cyclic nucleotide formed by bonding a cyclic nucleotide corresponding to the cyclic nucleotide to be assayed and an enzyme through a dicarboxylic acid to undergo a competitive antigen-antibody reaction with a predetermined quantity of an antibody corresponding to the cyclic nucleotide to be assayed;

separating the enzyme-labeled cyclic nucleotide which has become bonded to said antibody and the enzyme-labeled cyclic nucleotide which has not become bonded thereto; and measuring the enzyme activity of either of said enzyme-labeled cyclic nucleotides thereby to determine the quantity of the cyclic nucleotide.

2. The method as claimed in claim 1 in which the cyclic nucleotide is selected from the group consisting of adenosine-3',5'-cyclic monophosphate, guanosine-3',5'-cyclic monophosphate, inosine-3',5'-cyclic monophosphate, cytidine-3',5'-cyclic monophosphate, and uridine-3',5'-cyclic monophosphate.

3. The method as claimed in claim 1 in which the enzyme in the enzyme-labeled cyclic nucleotide is selected from the group consisting of $\beta$-D-galactosidase, peroxidase, alkaline phosphatase, glucose oxidase, glucoamylase, lysozyme, malate dehydrogenase, glucose-6-phosphate dehydrogenase, acetylcholine esterase, lipase, $\beta$-glucuronidase, hyaluronidase, $\beta$-glucosidase, and an active fragment of said enzyme.

4. The method as claimed in claim 1 in which the acylating agent is a combination of an acid anhydride and an organic tertiary amine.

5. The method as claimed in claim 4 in which the organic tertiary amine is selected from the group consisting of aliphatic tertiary amines and heterocyclic bases.

6. The method as claimed in claim 1 in which the antibody is selected from the group consisting of an antibody immobilized on an insoluble carrier and a soluble antibody.

7. The method as claimed in claim 6 in which the insoluble carrier is selected from the group consisting of silicone, glass, ceramics, polystyrenes, crosslinked polyacrylamides, plastics, CM cellulose, DEAE cellulose, cellulose, cross-linked dextran, filter paper and a carrier coated with an organic silane derivative.

8. A method according to claim 1 in which the cyclic nucleotide and acylating agent are reacted at room temperature for a period of 5 to 60 minutes and the antigen-antibody reactor proceeds at 1° to 5° C. for a period of 6 to 48 hours.

9. A kit for the quantitative analysis of cyclic nucleotides comprising, in combination, the following components each being in individual tubes:
 (a) an enzyme-labeled cyclic nucleotide;
 (b) an antibody to a cyclic nucleotide immobilized on an insoluble carrier;
 (c) an acid anhydride;
 (d) an organic tertiary amine;
 (e) a buffer solution;
 (f) a cyclic nucleotide standard solution;
 (g) an enzyme substrate; and
 (h) a reaction terminating agent;
said components (a) through (h) being present in amounts sufficient to perform the quantitative analysis of cyclic nucleotides according to the methods of any one of claims 1-7.

10. A kit for the quantitative analysis of cyclic nucleotides comprising, in combination, the following components each being in individual tubes:
 (a) an enzyme-labeled cyclic nucleotide;
 (b) an antibody to a cyclic nucleotide immobilized on an insoluble carrier;
 (c) an acid anhydride;
 (d) an organic tertiary amine;
 (e) a buffer solution;
 (f) a cyclic nucleotide standard solution;
 (g) an enzyme substrate;
 (h) a reaction terminating agent; and
 (i) a phosphodiesterase inhibitor;
said components (a) through (i) being present in amounts sufficient to perform the quantitative analysis of cyclic nucleotides according to the methods of any one of claims 1-7.

11. A kit for the quantitative analysis of cyclic nucleotides comprising, in combination, the following components each being in individual tubes:
 (a) an enzyme-labeled cyclic nucleotide;
 (b) an antibody to a cyclic nucleotide;
 (c) a separation agent;
 (d) an acid anhydride;
 (e) an organic tertiary amine;
 (f) a buffer solution;
 (g) a cyclic nucleotide standard solution;
 (h) an enzyme substrate; and
 (i) a reaction terminating agent;
said components (a) through (i) being present in amounts sufficient to perform the quantitative analysis of cyclic nucleotides according to the methods of any one of claims 1-7.

12. A kit for the quantitative analysis of cyclic nucleotides comprising, in combination, the following components each being in individual tubes:
 (a) an enzyme-labeled cyclic nucleotide;
 (b) an antibody to a cyclic nucleotide;
 (c) a separation agent;
 (d) an acid anhydride;
 (e) an organic tertiary amine;
 (f) a buffer solution;
 (g) a cyclic nucleotide standard solution;
 (h) an enzyme substrate;
 (i) a reaction terminating agent; and
 (j) a phosphodiesterase inhibitor;
said components (a) through (j) being present in amounts sufficient to perform the quantitative analysis of cyclic nucleotides according to the methods of any one of claims 1-7.

* * * * *